United States Patent [19]

Brinkhoff

[11] Patent Number: 4,564,009

[45] Date of Patent: Jan. 14, 1986

[54] UNIVERSAL EAR PLUG

[75] Inventor: Carl H. Brinkhoff, Pittsburgh, Pa.

[73] Assignee: Mine Safety Appliances Company, Philadelphia, Pa.

[21] Appl. No.: 525,988

[22] Filed: Aug. 24, 1983

[51] Int. Cl.[4] .............................................. A61F 11/02
[52] U.S. Cl. .................................................... 128/152
[58] Field of Search ................................. 128/152, 151

[56] References Cited

U.S. PATENT DOCUMENTS

| | | | |
|---|---|---|---|
| 2,393,005 | 1/1946 | Veneklasen | 128/152 |
| 3,415,246 | 12/1968 | Hill | 128/152 |
| 4,219,018 | 8/1980 | Draper, Jr. | 128/152 |

Primary Examiner—Henry J. Recla

[57] ABSTRACT

A universal ear plug that fits any size of ear, which may be worn for extended lengths of time without experiencing discomfort, comprising; an integral molded frustum-shaped, semi-rigid, solid body having an axial cavity in the tip end; a flexible flange around the hollow tip which extends outwardly from the tip towards the back; a second, larger, cup-shaped, semi-spherical flange positioned at the other end of the body; an axial mounted extraction and insertion stem attached along the outer rim of the second flange, which provides greater ease of insertion and removal.

2 Claims, 4 Drawing Figures

UNIVERSAL EAR PLUG

BACKGROUND OF THE INVENTION

This invention relates to a universal ear plug which fits any size ear and provides better performance and a greater noise reduction ratio.

Most molded earplugs which are available today are made in a number of sizes to fit different sized ears.

For example, Veneklasen, U.S. Pat. No. 2,393,005 discloses an ear plug with an outwardly extending flange at the tip of the plug which is inserted into the ear. The primary seal is made by a thin portion of a flexible tubular body, which seals against the outer edge of the ear canal. When the finger is pushed against the outer edge of the plug during insertion, the tubular body collapses causing the tip of the plug to enter the ear canal at an obtrusive angle. The tip of the plug protrudes relatively far into the ear canal, causing discomfort during extended periods of wear. Veneklasen's plug is made in a variety of sizes and must be inserted into the ear at the proper angle and position. It is often a laborious task to achieve a proper fit.

Another earplug is manufactured by Mine Safety Appliances Company, Pittsburgh, Pa. under the trademark "ACCU-FIT". The ACCU-Fit plug is comprised of a solid body portion with three outwardly extending flanges spaced lengthwise along the body. The first flange is located at the tip of the plug. This flange is the same as the flange used on Veneklasen's plug. The second flange is of greater diameter and is situated around the center of the body. The last flange is at the end of the plug and has the largest diameter. When inserted, one or more of the flanges will engage the ear canal depending on the ear size and the length of insertion. When inserted into a large ear, the plug protrudes quite far into the ear canal. This can result in discomfort during extended periods of wear. The ACCU-FIT plug has an extension of the central body portion which acts as the inserter. Since the plug is pushed from the center, the body sometimes distorts and the plug enters the ear canal at an angle. This can result in discomfort and diminished noise reduction.

Ear plugs using the post or body of the plug as the inserter, being of a soft material, also have a tendency to buckle or expand in the middle when pushed from the back end, as the front end resists being pushed into the ear. When the pushing stops, the expanded material relaxes tending to move the plug back out of the ear. This can cause improper sealing and diminished noise reduction.

SUMMARY OF THE INVENTION

It is the object of this invention to provide an ear plug that fits all normal ear sizes, is easy to insert, easy to remove and provides increased noise reduction ratios.

The ear plug of this invention, is comprised of a hollow tip surrounded by a swept-back flange. The flange is flared outward so that there is a large gap between the flange and the body of the plug. The body itself is frustum-shaped. The back portion of the body is comprised of a spherical cup-shaped flange which is of greater diameter than the tip flange. An extraction stem is attached, at the back of the plug, to the outer rim of the large flange, to permit removal of the plug.

The plug is inserted into the ear by grasping the extraction stem between the thumb and forefinger. The forefinger is automatically positioned in the center of the earplug and acts as an inserter. The short body of the plug remains rigid while exerting inward pressure. As the plug enters the ear canal, the edges of the flange are pushed inward against the body of the plug. The body of the plug prevents total inward collapse of the flanges by exerting outward lateral forces. The inward deformation of the plug is thus halted and the edges of the flange seal tightly against the walls of the ear canal.

No special orientation of the plug is required. While exerting inward pressure with the finger, the finger is moved up and down across the outer flange of the plug in a scratching motion. This walks the ear plug into the ear canal without buckling or expanding the body of the plug making it easier to insert and resulting in a better seal and higher noise reduction ratios. The user may wear the plug for extended periods of time because the plug protrudes into the ear only a short distance. The plug may be pushed into the ear until the ear canal engages the first flange, the second flange or both.

The universal ear plug fits securely into any size ear. When used in a small ear, the plug is inserted only as far as the first flange where the flange seals off the ear canal. As the size of the ear becomes larger, the plug may be inserted farther. In a medium-size ear, the plug will seal the ear canal at the first flange and at the outer flange. When uesd for a very large ear, the outer flange acts as the primary seal. Since the plug seals in this method, a higher noise reduction ratio is achieved and the ear plug may be used in noiser environments for longer periods of time.

The plug is made of a resilient material, such as rubber or a synthetic polymer, that is semi-rigid in thick cross sections and very flexible in thin cross sections.

DESCRIPTION OF THE PREFERRED EMBODIMENT

Figure 1:
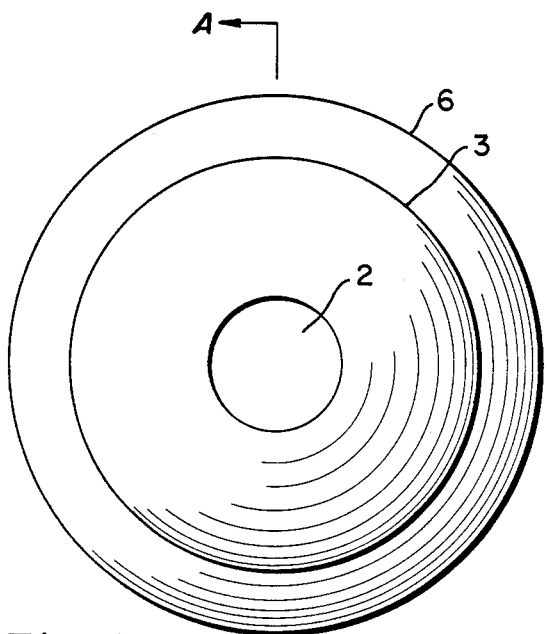
FIG. 1 is a frontal view of a preferred embodiment of the present invention.

With reference to FIGS. 1-4, the ear plug 1 comprises a hollow cavity 2 which permits the inner flange 3 to collapse inward into cavity 2 when inserted into smaller sized ears. Since the inner flange 3 is flared out at a greater distance 10 than most earplugs, the flange achieves a tighter seal in the ear canal 12. The body 4 is frustum-shaped and increases in diameter from the inner flange to the outer flange. The inner surface 5 of the flange 3 can conform to the tapered body 4 when the ear canal is very small. Because of the cavity 2, the shape of the flange 3, and the taper of the body 4, the earplug can be inserted into the ear canal 12 up to the point that the outer surface 7 of the rear flange 6 contacts the outer peripheral opening of the ear canal.

The ear plug need not be specially oriented before insertion into the ear. When inserted in to an ear 11, the plug will be pushed into the ear canal until flange 3 engages and seals inside the ear canal. When inserted into a medium size ear, the plug will slide farther into the ear canal and seal both at flange 3 inside the ear canal, and flange 6 at the ear opening. When inserted into a large size ear, the plug will seal at flange 6, just outside the ear opening. At no time will flange 6 or tab 8 ever slide into the ear itself. Since the plug is quite short in length, the plug protrudes only slightly into the ear canal.

The shape of the earplug 1 and the tab 8, which is offset from center, make the plug easy to insert. When the tab 8 is grapsed between the thumb and forefinger, the forefinger is automatically positioned in the center of the ear plug 9. While exerting inward pressure with the finger, the finger is moved up and down across the center of the ear plug 9 in a scratching motion. This walks the plug into the ear without buckling or expanding the body 4 of the plug. The tab 8 is on the edge of the outer flange 6. The tab could be positioned slightly off the edge, either inward or outward, and still achieve the same result. When the plug is firmly set in the ear canal 12, the tab protrudes from the ear to facilitate extraction.

Certain dimensions are preferred in construction of the plug to provide the best fit. The hollow opening 2 at the tip of the plug is about 0.13 inches in diameter. The main body of the plug 4 increases in diameter from about 0.19, suitably 0.188 inches, at the tip to approximately 0.31 inches, suitably 0.312 inches, at a point just before the outer flange 6. The length from the tip of the plug to the back of the first flange should be about 0.17 inches. The distance from the tip of the plug to the back of the second flange should be about 0.41 inches.

Figure 3:
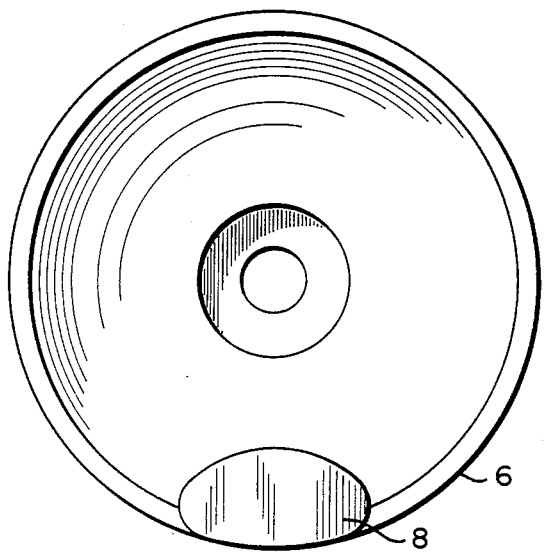
FIG. 3 is a rear view of the preferred embodiment of the present invention.
Figure 2:
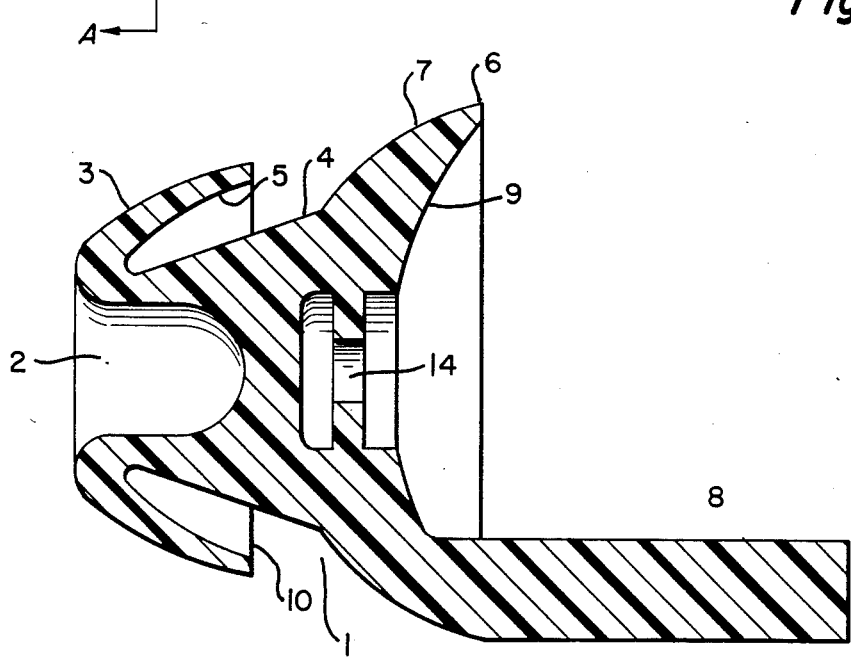
FIG. 2 is a cross section taken on line A—A in FIG. 1.
Figure 4:
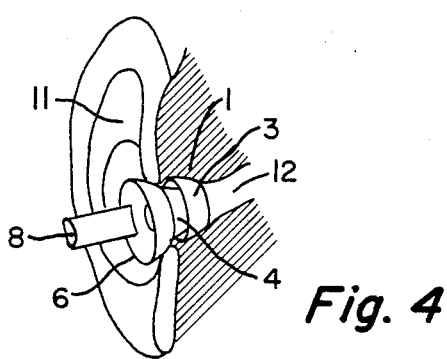
FIG. 4 is a detail vertical section of an ear canal illustrating the universal earplug inserted therein.

FIG. 3 shows a prefered location of the extraction tab 8 along the outer edge of the second flange 6.

The extraction cavity 14 is used to accept an extraction rod to remove the plug from a mold following the manufacturing process. It does not significantly affect the rigidity of the body 4 and serves no other purpose.

This description is to be construed as illustrative only, and it is to be understood that the terms of the invention herewith shown and described are to be taken as the presently preferred embodiments. It is intended that the following claims be interpreted to embrace all modifications and changes which may become apparent to those skilled in the art.

I claim:
1. An integral molded ear plug comprising:
   a frustum-shaped, non-deformable in use, semirigid main body which increases in diameter from its tip end to its back end and having an axial cavity in the tip end;
   a flexible front flange of circular cross section extending outwardly from the tip end and rearwardly over a portion of the distance of the main body and terminating in a rim spaced from the back end, and having a diameter that is greater than the major diameter of the main body;
   a second, cup-shaped, semi-spherical flange extending radially outwardly from the back end and rearwardly of the main body and terminating in a rim, and having a diameter greater than the diameter of the front flange; and
   an extraction tab extending rearwardly from the rim of the second flange.
2. An ear plug according to claim 1 where:
   the axial cavity is about 0.13 inches in diameter;
   the frustum-shaped body of the plug increases in diameter from about 0.19 inches at the tip to about 0.31 inches at the back;
   the length from the tip to the edge of the first flange is about 0.17 inches; and
   the distance from the tip of the plug to the rim of the second flange is about 0.41 inches.

* * * * *

UNITED STATES PATENT OFFICE
CERTIFICATE OF CORRECTION

PATENT NO. : 4,564,009

DATED : January 14, 1986

INVENTOR(S) : Carl H. Brinkhoff

It is certified that error appears in the above-identified patent and that said Letters Patent are hereby corrected as shown below:

On the title page,
    [73] Assignee: Change Philadelphia, Pa. to Pittsburgh, Pa.

Signed and Sealed this

Fifteenth Day of April 1986

[SEAL]

Attest:

DONALD J. QUIGG

Attesting Officer     Commissioner of Patents and Trademarks